US009616094B2

(12) United States Patent
Schiffrin

(10) Patent No.: US 9,616,094 B2
(45) Date of Patent: *Apr. 11, 2017

(54) PROBIOTICS IN A PRE- AND/OR POST-SURGICAL ENVIRONMENT

(71) Applicant: NESTEC S.A., Vevey (CH)

(72) Inventor: Eduardo Schiffrin, Crissier (CH)

(73) Assignee: Nestec S.A., Vevey (CH)

( * ) Notice: Subject to any disclaimer, the term of this patent is extended or adjusted under 35 U.S.C. 154(b) by 224 days.

This patent is subject to a terminal disclaimer.

(21) Appl. No.: 13/974,693

(22) Filed: Aug. 23, 2013

(65) Prior Publication Data
US 2013/0344044 A1 Dec. 26, 2013

Related U.S. Application Data

(63) Continuation of application No. 12/598,905, filed as application No. PCT/EP2008/055898 on May 14, 2008, now Pat. No. 8,529,887.

(30) Foreign Application Priority Data

May 18, 2007 (EP) ..................................... 07108492

(51) Int. Cl.
A61K 35/745 (2015.01)
A61K 35/747 (2015.01)
A23L 33/135 (2016.01)

(52) U.S. Cl.
CPC .......... A61K 35/747 (2013.01); A23L 33/135 (2016.08); A61K 35/745 (2013.01)

(58) Field of Classification Search
CPC .. A61K 2300/00; A61K 35/74; A61K 35/747; A61K 38/1841; A61K 36/064; A61K 38/162; A61K 38/2013; A61K 38/2066; A61K 38/208; A61K 35/745; A61K 31/715; A61K 33/24; A61K 33/26; A61K 45/06; A61K 35/744; A61K 36/00; A61K 38/13; A61K 2035/115; A61K 2800/70; A61K 35/742; A61K 8/99; A61K 31/202; A61K 31/702; A61K 31/733; A61K 31/736; A61K 36/07; A61K 36/77; A61K 31/00; A61K 31/355; A61K 31/56; A61K 31/663; A61K 31/07; A61K 38/22; A61K 38/225; A61K 31/4164; A61K 31/43; A61K 31/496; A61K 31/65; A61K 31/7036; A61K 31/164; A61K 31/19; A61K 31/395; A61K 31/437; A61K 31/7048; A61K 33/04; A61K 31/12; A61K 36/185; A61K 33/00; A23L 1/3014; A23L 1/301; A01N 63/00
See application file for complete search history.

(56) References Cited

U.S. PATENT DOCUMENTS

| | | | |
|---|---|---|---|
| 5,578,302 A | 11/1996 | Brassart et al. | |
| 5,603,930 A * | 2/1997 | Brassart | A23C 9/1234 424/93.45 |
| 7,217,414 B2 * | 5/2007 | Schiffrin | A23L 1/0345 424/9.1 |
| 7,468,270 B2 | 12/2008 | Xaus Pei et al. | |
| 7,595,079 B2 * | 9/2009 | Lall | A61K 35/744 424/400 |
| 7,678,370 B2 * | 3/2010 | Schiffrin | A23L 1/0345 424/9.1 |
| 7,862,808 B2 * | 1/2011 | Isolauri | A23L 33/135 424/93.3 |
| 8,394,370 B2 * | 3/2013 | Garcia-Rodenas | A23L 1/296 424/93.45 |
| 8,529,887 B2 * | 9/2013 | Schiffrin | 424/93.44 |
| 2002/0127211 A1 | 9/2002 | Brassart et al. | |
| 2003/0092163 A1 | 5/2003 | Collins et al. | |
| 2004/0005305 A1 | 1/2004 | Spivey-Krobath et al. | |
| 2005/0123527 A1 | 6/2005 | Conte | |

FOREIGN PATENT DOCUMENTS

| | | |
|---|---|---|
| EP | 0861905 | 9/1998 |
| JP | 10191916 | 7/1998 |
| RU | 2293568 | 2/2007 |
| WO | WO9907393 | 2/1999 |
| WO | WO0178533 | 10/2001 |
| WO | 2006046871 | 5/2006 |
| WO | WO2006046871 | 5/2006 |

OTHER PUBLICATIONS

Database WPI Week 200726, Thomson Scientific, AN 2007-266790, XP002452342 & RU 2 293 568 C1 (Krylof), Feb. 20, 2007, Abstract Only.
Seehofer et al. "Probiotics partly reverse increased bacterial translocation after . . . " Journal of Surgical Research, XP002322829, Apr. 2004; vol. 117, No. 2, pp. 262-271.
Besselink et al. "Prevention of infectious complications in surgical patients: potential role of . . . " Digestive Surgery, XP009089653, 2005; vol. 22, No. pp. 234-244.
Rayes et al. "Early enteral supply of Lactobacillus and fiber versus selective bowel . . . " Transplantation, XP002452299, Jul. 15, 2002; vol. 74, No. 1, pp. 123-128.
Schiffrin et al. "Immune modulation of blood leukocytes in humans by lactic acid bacteria: criteria for . . . " Am. J. Clin. Nutr., XP002194826, 1997; vol. 66, pp. 515S-520S.
Neeser et al. "Lactobacillus johnsonii La1 shares carbohydrate-binding specificities with several enteropathogenic bacteria" Glycobiology, vol. 10. No. 11, 2000, pp. 1193-1199.

(Continued)

Primary Examiner — Debbie K Ware
(74) Attorney, Agent, or Firm — K&L Gates LLP

(57) ABSTRACT

The present invention relates generally to the field of nutrition, more particularly to the use of probiotics in nutrition. In particular the present invention relates to the use of a probiotic or of a mixture of probiotics in the manufacture of a nutritional composition or a medicament to act the colon in a pre- or post surgical environment.

20 Claims, 1 Drawing Sheet

(56) References Cited

OTHER PUBLICATIONS

Abstract of Goossens et al. "The effect of a probiotic drink with Lactobacillus plantarum 299v on the bacterial composition in faeces and mucosal biopsies of rectum and ascending colon" Ailment Pharmacol Ther, Jan. 15, 2006; 23 (2); pp. 255-263 (1 page Abstract).

Burbello et al. "Modern pharmacological products" Clinico-Pharmacological Manual—Chapter 4, 3rd Edition, St. Petersburg, Neva Publishing House, p. 202.

Grigoriev et al. "Practical application of Bifidumbacterin Forte in pediatric surgery" AO Partner, Moscow, NII PAT of Academy of Medical Sciences, Ukraine, New Pharmaceutical Preparation, M, No. 1, 1996.

Large Encyclopaedia, vol. 21, Moscow, Terra, 2006.

Large Encyclopaedia, vol. 33, Moscow, Terra, 2006.

\* cited by examiner

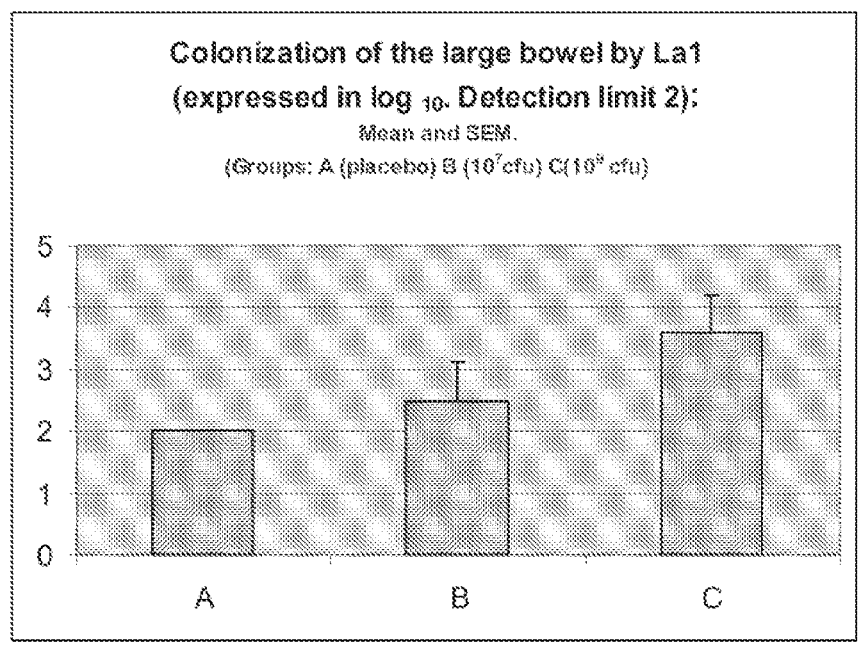

PROBIOTICS IN A PRE- AND/OR POST-SURGICAL ENVIRONMENT

PRIORITY CLAIM

This application is a continuation of U.S. application Ser. No. 12/598,905, filed Nov. 4, 2009, which is a National Stage of International Application No. PCT/EP2008/055898 filed May 14, 2008, which claims priority to European Patent Application No. 07108492.5, filed May 18, 2007, the entire contents of which is incorporated herein by reference thereto

BACKGROUND

The present invention relates generally to the field of nutrition, more particularly to the use of probiotics in nutrition and in particular to the use of probiotics in nutrition in a pre- and/or post-surgical environment.

As early as 1907, the Russian scientist, E. Metchnikoff (1845-1919), working at the Pasteur Institute in Paris, published work showing the beneficial effects of lactic acid bacteria contained in yogurt. Metchnikoff hypothesized that a high concentration of lactobacilli in the intestinal flora might be important for health and longevity in humans (Metchnikoff E M, et al., The prolongation of life: optimistic studies. London: Heinemann 1907; 161-183).

Since this time no other group of bacteria has been proposed to be responsible for so many different beneficial effects as lactic acid bacteria, mainly lactobacilli and *Bifidobacteria*. These include the stimulation of macrophage phagocytosis of viable *salmonella* (Hatcher G et al., J. Dairy. Sci. 1993; 76:2485-2492); the enhancement of IgA production in intestinal secretions (Perdigon G, et al., J. Food. Proct. 1990; 53:404-410), production of antimicrobial substances (Shahani K M, et al., Am. J. Clin. Nutr. 1980; 33:2448-2457; Silvia M, et al., Antimicr. Agen. Chemother. 1987; 31:1231-1233); the inhibition of cell attachment and cell invasion by enterovirulent bacteria (Bernet M F, et al., Gut 1994; 35:483-489) and the reduction of intestinal permeability to macromolecules during rotavirus induced diarrhea (Isolauri E, et al., Pediatr Res 1993; 33:548-553). *Lactobacillus* bacteria have also been used with success in the treatment of relapsing *Clostridium difficile* colitis (Gorbach S L, et al., Lancet 1987; 2:1519).

These beneficial properties are not shard by all *Lactobacillus* and *Bifidobacteria* strains. Lactic acid bacteria that show a beneficial biological activity are considered to be probiotics. However, not all probiotics share the same type of beneficial biological activities. One example of a *Lactobacillus* strain that belongs to the group of probiotics is the *Lactobacillus johnsonii* (La1) organism (Nestle. *Lactobacillus johnsonii* (La1) Scientific Overview; 1999). This strain was isolated several years ago from the human intestinal flora at the Nestle Research Center in Lausanne.

The La1 bacteria can be considered as a probiotic because the strain is

Non-pathogenic

Remains viable on reaching the small intestine or the colon

Shows good adhesion to the intestinal mucosal membrane

Is a natural component of the human intestinal flora

In addition, research has demonstrated that La1 bacterial strain possesses some other beneficial properties including:

Inhibition of the adherence of several enteropathogenic bacteria (*E Coli* ssp and *Salmonella* spp) to human intestinal cells in vitro Anti-diarrheal effects and inhibition of invasive *E Coli* species Effect on the prevention of *H. pylori*-associated diseases Stimulation of immune defenses Stimulation of phagocytosis Stimulation of IgA production Antagonism of colonization by *Clostridium perfringens*

The La1 bacteria strain is presently used in fermented milk specialities (Nestle LC1 product range) which are widely marketed in Europe as a new concept in healthy eating. No adverse events have been documented when used by the general population, and the La1 probiotic strain can thus be considered as safe.

The administration of probiotic bacteria in general has been hypothesized to affect the composition of the intestinal microflora with reduction of pathogens in favour of non-pathogens. These events might modulate the immune and inflammatory responses and the gut function. (Liopis, M, et al., Gut 2005 54: 955-959).

Experimental data demonstrated that the modulation of the mucosal function and enteric microflora by *Lactobacillus plantarum* reduces septic morbidity and mortality in animals. The administration of a mix of probiotics has been shown to be more effective than antibiotics to cure pouchitis in humans (Gionchetti, Paolo et al., Gastroenterology 2003, 124:1202-9.)

While the positive effects of probiotics as an aspect of modern nutrition today under normal living circumstances are widely accepted, the use of probiotics as a part of nutrition in a pre- and/or post clinical environment has never been suggested.

One reason for this might be that is commonly known that surgery should take place under sterile conditions. The consumption of bacteria as preparation for surgery and briefly after surgery appears to be contradictory to the recommended sterility.

Usually, and in stark contrast to healthy people under normal living conditions, people in a pre- or post clinical environment usually are under a significant amount of stress, are under heavy antibiotic treatment, might suffer from an impaired immune system and/or are at a significant danger of being colonized by pathogenic and antibiotic resistant bacteria that appear more and more often in repeatedly sterilized environments such as hospitals.

Consequently, a pre- and/or post clinical environment cannot be compared to normal living circumstances.

Since, however, patients undergoing surgery have a high risk of developing infections, e.g., due to intraoperative contamination with enteral contents and the occurrence of bacterial translocation, it would be desirable to have available a method that allows to prevent and/or to reduce of such complications and post operative sepsis.

SUMMARY

Based on this state of the art it was the object of the present invention to provide the art with a method to prepare a patient as well as possible for the special conditions in a pre- and/or post-surgical environment.

This object is solved by a use in accordance with claim 1.

In particular the present inventors have unexpectedly discovered that a probiotic or a mixture of probiotics can be used in the manufacture of a nutritional composition or a medicament to act on the colon in a pre- or post-surgical environment.

BRIEF DESCRIPTION OF THE DRAWINGS

FIG. 1 shows the level of colonization of the large bowel by *Lactobacillus johnsonii* La1, expressed in a $\log_{10}$ scale, from the experimental study disclosed herein.

DETAILED DESCRIPTION

A probiotic is for the purpose of the present invention a micro-organism, dead or alive or a fraction thereof, which when administered in adequate amounts confers a health benefit on the host. Preferably, probiotics are live micro-organisms which when administered in adequate amounts confer a health benefit on the host.

A nutritional composition is for the purpose of the present invention a nutritional balanced formulation containing adequate proportions of macro- and micronutrients. Those skilled in the art will understand that the composition of the nutritional balanced formulation will depend on a number of factors, such as age, sex, and condition of the subject to be treated. However, those skilled in the art will be able to determine the composition of the formulation appropriately.

In the framework of the present invention the way by which the probiotics act on the colon is not particularly limited. If dead probiotics are used, these could act on the distal small bowel and the proximal colon, e.g., by releasing a significant quantity of bacterially associated molecular patterns that can stimulate the immune response and promote an homeostatic modulatory condition at the distal intestinal mucosa. Thus bacterial products or conserved molecules will interact principally with host cell receptors on the epithelial and dendritic cells of the mucosal compartment (S. Rakoff Nahoum, et al., Cell. 2004 118:229-241).

In contrast, living probiotics could act on the colon by passing through it. Possible effects produced by viable probiotics passing through the colon can be exerted by their capacity to expand and thereby to compete for available habitats in the distal intestinal environment and to displace of pathogenic bacteria; in addition or alternatively—as they remain metabolically active—they can prevent overgrowth of pathogens due to metabolic products such as short chain fatty acids and the release of bioactive molecules that can have bacteriostatic or bactericidal activity against other bacteria. Furthermore live bacteria and the molecules released as a consequence of their metabolic activity or natural cell death have the capacity to interact with the host immune molecules expressed on the surface of the mucosa and thereby stimulate an immune response or induce a cytoprotective reaction of the mucosal cells.

Preferably, however, the probiotics reach the colon alive and colonize it. This way, they establish a permanent presence and can produce a much more pronounced effect. In particular, the probiotics that establish a local presence by colonization are effective in changing the ecological situation of the colon by their metabolic activity.

Hence in one preferred embodiment of the present invention the probiotics act by a reaching the colon alive, in particular by colonizing the colon.

If probiotics colonize the colon they preferably colonize the colonic lumen and mucosal surfaces. This way they can produce the most pronounced effect.

A consequence of the effect of probiotics on the colon is that non-infectious diarrhea can be prevented and/or managed by the nutritional composition or medicament prepared by the use of the present invention.

A further consequence of this effect on the colon is that postsurgical abdominal-pelvic infections due to pelvic fluid collection secondary to leakiness in the anastomosis or bacterial translocation can be prevented by the nutritional composition or medicament prepared by the use of the present invention.

A further consequence of this effect on the colon is that gastrointestinal symptoms secondary to global changes in the intestinal microbial ecology and the microbiota metabolic activity, preferably infectious or toxigenic diarrhea can be prevented and/or alleviated by the nutritional composition or medicament prepared by the use of the present invention. The disturbance of normal gastrointestinal flora, particularly after antibiotic use and/or colonic surgery, is believed to predispose patients to colonization by *C. difficile*. The nutritional composition or the medicament of the present invention containing selected probiotics that can colonize the colon, in particular the colonic lumen and/or mucosal surfaces, can restore the equilibrium in the altered gastrointestinal flora and thus protect against colonization or bacterial overgrowth of potentially pathogenic bacteria.

A further consequence of this effect on the colon is that gastrointestinal infections, preferably nosocomial gastrointestinal infections can be prevented or treated by the nutritional composition or medicament prepared by the use of the present invention. Such gastrointestinal infections are often times responsible for the appearance of diarrhea, which consequently, can be prevented and or treated in accordance with the present invention.

Furthermore, the nutritional composition or the medicament prepared by the use of the present invention can advantageously be used for the prevention of nosocomial colonization by methicillin-resistant *Staphylococcus aureus* and vancomycin-resistant enterococci or other antibiotic resistant micro-organisms in the nosocomial environment.

In particular, according to the present invention probiotics can be used in the manufacture of a nutritional composition and/or of a medicament to modulate, in particular increase, the inflammatory response, in particular during the healing process. This effect of the products obtainable by the use of the present invention can be achieved, e.g., by stimulating the production of mucosal secretory antibodies.

The nutritional composition and/or the medicament prepare by the use of the present invention can be used for modulating the immune system and/or for stimulating the production of mucosal secretory antibodies.

The kind of probiotics usable in the present invention is not particularly limited. Any known probiotic is applicable.

However, preferably the probiotic is selected from the group consisting of *Bifidobacterium*, *Lactobacillus*, *Streptococcus* and *Saccharomyces* or mixtures thereof; more preferably the probiotic is selected from the group consisting of *Bifidobacterium longum*, *Bifidobacterium lactis*, *Lactobacillus acidophilus*, *Lactobacillus rhamnosus*, *Lactobacillus johnsonii*, *Lactobacillus plantarum*, *Lactobacillus salivarius*, *Streptococcus faecium*, *Saccharomyces boulardii* and *Lactobacillus reuteri* or mixtures thereof; and most preferred the selected probiotic is selected from the group consisting of *Lactobacillus johnsonii* La1 (CNCM I-1225), *Bifidobacterium longum* (CNCM I-2170), *Bifidobacterium lactis* Bb12 (German Culture Collection: DSM20215), (*Lactobacillus paracasei* (CNCM I-2116, CNCM I-1292)), *Lactobacillus rhamnosus* GG, *Streptococcus faecium* SF 68, and mixtures thereof.

CNCM I-1225, CNCM I-2116, CNCM I-2170 and CNCM I-3446 were deposited according to the Treaty of Budapest with the Pasteur Institute (28 rue du Doctor Roux, F-75024 Paris cedex 15) on Jun. 30, 1992; Jan. 12, 1999; Apr. 15, 1999 and Jun. 7, 2005, respectively.

In one embodiment of the present invention, the nutritional composition and/or the medicament further comprises additional non-viable probiotic bacteria and/or probiotic-derived material. Probiotic derived material can be any material that is derived from the probiotics themselves, such as, e.g., a cellular fraction or a compound or a group of compounds isolated from probiotics; or it can be material that was produced with the help of probiotics, such as culture medium or a part thereof, where probiotics were cultivated or a product that was modified with the help of probiotics; or a mixture thereof.

Preferably the nutritional composition and/or the medicament prepared by the use of the present invention further comprises fermentation substrate of the probiotics. It was found that this supports the viability of the probiotics, e.g., during storage times.

In one embodiment of the present invention the composition and/or the medicament prepared by the use of the present invention further comprises one or more prebiotics. Prebiotics are for the purpose of the present invention non-digestible food ingredients that beneficially affect the host by selectively stimulating the growth and/or activity of one or more bacteria in the colon.

Prebiotics have the advantage that they support the growth of beneficial bacteria in the colon of the patient. They furthermore support the viability of living probiotics present in the composition and/or the medicament prepared by the use of the present invention, both during storage times and after consumption by the patient.

A patient can be a human or an animal. Preferred animals are pet animals and livestock.

In one embodiment of the present invention, the nutritional composition and/or the medicament prepared by the use of the present invention comprises probiotics in an amount of about $10^5$-$10^{11}$ cfu/ml, preferably about $10^6$-$10^9$ cfu/ml, most preferred about $10^7$-$10^8$ cfu/ml. It is to understood, however, that the optimal amount of probiotics is to be determined by medical personal, since this depends on numerous factors, such as, e.g., the kind, age, sex, condition, body weight of the patient as well as on the nature of the product. Usually, medicaments will contain higher amounts of probiotics than nutritional compositions. In general any amount of probiotics will produce a beneficial effect.

The composition of the present invention comprises in one embodiment further a carbohydrate source, a lipid source and/or a protein source.

The composition of the present invention is to be understood as the nutritional composition and/or the medicament prepared by the use of the present invention.

The nutritional composition and/or the medicament may include a lipid source.

Preferably the lipid source provides about 18% to about 50% of the energy of the nutritional composition, more preferably about 25% to about 35% of total energy of a nutritional composition, most preferably about 30% of total energy of the composition.

The lipid source may include medium chain triglycerides (MCT), for example up to a level of 20% of the total lipid by weight. Such medium chain triglycerides are easily absorbed and metabolized in the acutely ill, catabolic patient. In a preferred embodiment, the medium chain triglyceride source is fractionated coconut oil.

The lipid profile may also comprise a mixture of long chain triglycerides. Suitable sources of long chain triglycerides are canola oil, corn oil, soy lecithin and residual milk fat. The lipid source may also contain polyunsaturated fatty acids. Preferably the lipid source contains about 15% to about 30% by weight of polyunsaturated fatty acids, for example about 20% by weight of polyunsatured fatty acids.

The lipid profiles containing long chain triglycerides are designed to have a polyunsaturated fatty acid omega-6 (n-6) to omega-3 (n-3) ratio of approximately 1:1 to 10:1. Preferably, the n-6 to n-3 fatty acid ratio is about 5:1 to about 9:1; for example about 7:1. The proposed ratio of n-6:n-3 is designed to reduce the immune suppression associated with high omega-3 fatty acid concentration and to provide adequate essential fatty acids. In an embodiment, the composition includes an omega-6 to omega-3 ratio of 7.7:1.

The lipid source is preferably rich in monounsaturated fatty acids. In particular, the lipid source contains at least about 40% by weight of monounsaturated fatty acids. Preferably, the lipid source contains about 45% to about 65% by weight of monounsaturated fatty acids; for example about 55% by weight.

The lipid source has preferably a saturated fatty acid content of less than about 35% by weight; including medium chain triglycerides. More preferably, the lipid source contains less than about 30% by weight of saturated fatty acids.

Suitable lipid sources include high oleic sunflower oil, high oleic safflower oil, sunflower oil, safflower, rapeseed oil, soy oil, olive oil, canola oil, corn oil, peanut oil, rice bran oil, butter fat, hazelnut oil and structured lipids. Fractionated coconut oils are a suitable source of medium chain triglycerides.

The lipid source may also contain vitamin E, preferably at least about 30 mg of vitamin E per 100 g of lipid source.

The nutritional composition and/or the medicament may include a carbohydrate source.

Preferably the carbohydrate source comprises maltodextrin, corn syrup, corn starch, modified starch, or sucrose, or fructose, or mixtures thereof. The carbohydrate source preferably provides at least about 15%, preferably about 20%-40%, of the total calories of the composition, or about 40% to about 65% of the energy of the nutritional supplement; especially about 50% to about 60% of the energy of the nutritional composition. For example, the carbohydrate source may provide about 54% of the energy of the supplement.

If desired, the nutritional composition and/or the medicament may be free from lactose.

E.g., to avoid occurrence of diarrhea the composition may also contain a dietary fibre, preferably in an amount of at least 8 g/l, most preferably in an amount of at least 14 g/l.

Hence, preferably the nutritional composition and/or the medicament further includes a source of a soluble, prebiotic fibre. A prebiotic fibre is a fibre which beneficially affects the host by selectively stimulating growth and/or activity of bacteria in the colon which have the potential to improve host health. Suitable soluble, prebiotic fibres include fructooligosaccharides (FOS) and inulin. Suitable inulin extracts may be obtained from Orafti SA of Tirlemont 3300, Belgium under the trade mark "Raftiline". Similarly, suitable fructooligosaccharides may be obtained from Orafti SA of Tirlemont 3300, Belgium under the trade mark "Raftilose".

Preferably, both FOS and inulin are provided in a ratio of about 60:about 40 to about 80:about 20, most preferably about 70:about 30. Other possible fibres include gums such as guar gum, xanthan gum, xylo-oligosaccharides, gum arabic, pectin, acacia gum, resistant starch, dextrans or mixtures of these. The fibre selected should preferably not induce satiety.

The soluble, prebiotic fibres are reported to promote the growth of *Bifidobacteria* in the gastrointestinal tract and, in certain circumstances prevent or decrease the growth of pathogens such as Clostridiae. Further, promoting the growth of *Bifidobacteria* is reported to have various other beneficial effects. Also, during fermentation of the fibres in the colon, short chain fatty acids are produced. These fatty acids are a fuel for intestinal cells.

The soluble, prebiotic fibres are preferably present in an amount sufficient to provide about 4 to about 9 g of soluble, fermentable fibre to the patient per day. Therefore the prebiotic fibres may be present in an amount of about 6 g to about 12 g per 1000 kcal. Alternative embodiments comprise blends of prebiotic fibres in an amount of 9 g or less, for example 4 g of blend.

If desired, the nutritional supplement may also contain a source of insoluble dietary fibre. Suitable sources of insoluble dietary fibres are hull fibres from legumes and grains; for example pea hull fibre, oat hull fibre, barley hull fibre, and soy hull fibre.

Similarly, the osmolality of the nutritional composition can be adjusted to the intended purpose, e.g., to avoid diarrhea, in particular to be less than 500 mOsm, more preferred to be less than 300 mOsm, e.g., to an osmolality of about 100 to 250 mOsm. Flavoured products usually have a higher osmolality than unflavoured products.

The nutritional composition and/or the medicament may include a protein source.

The protein source may include at least about 50% by weight of whey protein that preferably has been at least partially hydrolyzed. The whey protein used to produce the hydrolysate may be a commercially available whey protein source; either based upon sweet whey or acid whey or a combination thereof. Preferably the whey protein is a whey protein source containing more than 80% by weight of whey protein. A suitable whey protein concentrate is LACPRO-DAN 9087 and suitable whey protein isolate sources include ALACEN 895 (New Zealand Milk Products Inc), BiPRO (LeSueur Isolates of Le Sueur, Minn.), PROVON-190 (Avonmore Ingredients Inc of Monroe Wis.) and LACPRO-DAN 9212 (Royal Proteins, Inc of Rosemont Ill.).

The protein source may, if desired, include amounts of other suitable types of protein. For example, the protein source may further include minor amounts of casein protein, soy protein, rice protein, pea protein, carob protein, oat protein, milk protein, caseino-glyco-macropeptide or mixtures of these proteins. Further, if desired, the protein source may further include minor amounts of free amino acids. The other suitable types of protein preferably comprise less than about 50-% by weight of the protein source; more preferably less than about 30% by weight.

Depending on the condition the patient is in, the protein source is preferably selected so that the resulting food composition is easy to digest.

A high protein concentration may be used to provide sufficient protein to replete lean body mass in patients with elevated protein losses. Elevated protein requirements have been identified in patient populations such as pressure ulcer, serious wounds, trauma, Crohn's disease with protein-losing enteropathy, chronic diarrhea, and HIV/AIDS malabsorption and diarrhea. Inherent to the metabolic requirements of these conditions is an increased loss of nitrogen, increased requirement for protein or both.

The composition of the present invention may be designed to be a peptide-based diet. In choosing the protein source, the present invention maximizes tolerance and absorption with the use of a hydrolyzed protein. In a preferred embodiment, the protein source is enzymatically hydrolyzed whey protein. This type of protein source reduces the incidence of gastric reflux because gastric emptying is faster than with diets containing casein or whole whey. Also, hydrolyzed whey protein serves as a rich source of the amino acid cysteine, which is a limiting amino acid for the formation of glutathione.

The protein source preferably provides about 8% to about 25% of the energy of the nutritional supplement. According to one embodiment of the present invention the protein source provides at least about 8%, preferably about 15%-25%, of the total calories of the composition. For example, the protein source may provide about 15% to about 18% of the energy of the composition in an embodiment suitable for an adult or about 8% to about 14% of the energy of the supplement in an embodiment suitable for pediatric use.

In a particular preferred embodiment of the present invention the protein source provides at least about 8%, preferably about 15%-25%, of the total calories of the composition, the lipid source provides at least about 18%, preferably about 30%-50%, of the total calories of the composition and preferably has an omega 6 to omega 3 fatty acid ratio of approximately 2:1 to about 10:1, and the carbohydrate source provides at least about 15%, preferably about 20%-40%, of the total calories of the composition.

In one embodiment of the present invention the nutritional composition or the medicament further comprises micronutrients, preferably selected from the group consisting of comprising at least vitamin E and vitamin C.

Even more preferred the nutritional composition and/or the medicament comprises a complete vitamin and mineral profile. For example, sufficient vitamins and minerals may be provided to supply about 50% to about 500% of the recommended daily allowance of the vitamins and minerals per 1000 calories of the nutritional supplement. The nutritional composition and/or the medicament preferably is rich in vitamin E. For example, the nutritional composition and/or the medicament may contain between 80 International Units and 120 International Units of Vitamin E per 1000 kcal. More preferably, the nutritional supplement contains about 30 International Units of Vitamin E per 250 ml serving of the supplement.

Furthermore the nutritional composition and/or the medicament is also rich in Vitamin C providing between about 150 and about 250 mg per 1000 kcal or preferably about 60 mg per serving. Vitamin C is believed to accelerate the healing and granulation in patients with severe healing requirements. Vitamin C will support increased requirements/losses after surgery.

The nutritional composition and/or the medicament also preferably contains 200 g of folic acid and 3 g of Vitamin B-12 per dosage form. Alternative embodiments of the nutritional composition and/or the medicament for pediatric use have a modified vitamin and mineral profile specifically tailored to the special needs of this age group.

Pursuant to the present invention, the composition may also include a high level of zinc. Preferably, at least approximately 150% of the USRDA of zinc is provided in the composition per 1000 Kcal. In an embodiment, 19 to 29 mg per 1000 calories of zinc are provided. In a preferred embodiment, 24 mg per 1000 calories of zinc is provided. The increased zinc compensates for zinc losses and provides increased zinc for tissue repair in a patient having increased healing requirements.

Pursuant to the present invention, the composition may also include increased amounts of selenium. Selenium deficiencies may develop in patients having elevated healing requirements. Pursuant to the present invention, at least approximately 40 to 60 μg of selenium are provided in 1000 calories of formula. In a preferred embodiment, approximately 50 µg of selenium per 1000 calories is provided.

The composition of the present invention may also include a source of beta-carotene. Beta-carotene can be added to the composition to normalize beta-carotene serum plasma levels and avoid beta-carotene deficiency in long term tube-fed patients. The composition preferably includes approximately 1.6 to 2.4 mg per 1000 calories. This amount prevents deficiencies and provides for possible increased requirements in the healing patient. Moreover, the beta-carotene levels allow plasma concentrations to be increased to near normal optimal levels of 500 mcg per liter.

The composition of present invention may also provide increased amounts of L-carnitine and taurine to support the increased requirements of the acutely ill, catabolic patient. Both taurine and L-carnitine are preferably present in amounts of approximately 80 to 120 mg per 1000 calories. In preferred embodiments, both taurine and L-carnitine are present in an amount of approximately 100 mg per 1000 calories.

Still further, the composition of the present invention includes decreased amounts of magnesium. Magnesium has been associated with diarrhea. In an embodiment, magnesium is present in an amount of approximately 237 mg to 355 mg per 1000 calories. In a preferred embodiment, magnesium is present in an amount of approximately 300 mg per 1000 calories.

The nutritional composition of the present invention preferably has an energy content of about 800 kcal/1 to about 2000 kcal/1; for example an energy content of about 1000 kcal/1 or about 1500 kcal/1. Preferably, the caloric density of the composition is 1.0 kcal/ml.

The nutritional composition and/or the medicament may be in the form of a soluble powder, a liquid concentrate, a pudding, a bar/snack or a ready-to-use formulation suitable for oral consumption or enteral administration. Ready to drink formulations are particularly preferred. Various flavours, sweeteners, and other additives may also be present. Artificial sweeteners such as acetosulfame and L-aspartyl based sweeteners may be used; for example acesulfame-K or aspartame or a mixture thereof.

The composition of the present invention is preferably a ready-to-use enteral formulation. The composition can be used as a supplement or for total enteral nutritional support. The composition can be tube-fed to a patient, or fed by having the patient drink same.

The amount of the nutritional composition and/or the medicament required to be fed to a patient will vary depending upon factors such as the patient's condition, the patient's body weight, the age of the patient, and other sources of nutrition. However the required amount may be readily set by a medical practitioner. The nutritional supplement may be taken in multiple doses, for example 2 to 5 times, to make up the required daily amount or may be taken in a single dose.

Those skilled in the art will understand that they can combine any features described in this specification without departing from the scope of the invention as disclosed.

Further embodiments and advantages of the present invention will be evident from the following Examples and Figures.

FIG. 1 shows the level of colonization of the large bowel by *Lactobacillus johnsonii* La1 expressed in la log io scale. Displayed are mean values and the corresponding standard derivations for group A (placebo), group B ($10^7$ cfu) and group C ($10^9$ cfu).

Example 1

The intestinal microbiota comprises an extremely high number of microbes of different cell lineage that can communicate with each other and the host. Overall the microbiota is a real organ that is implicated in a multitude of functions that contributes to the health of the host. It recovers energy from complex carbohydrates that escape the digestion of host enzymes in the small bowel, it plays an important role in the prevention of colonization by pathogenic bacteria and it contributes to preserve the mucosal barrier and to modulate the inflammatory/immune reactivity of the mucosa. Interestingly after subtotal and total colectomy the metabolic and protective activities of the microbiota are decreased and therefore post surgical complications can be enhanced due to the transient impaired microbiota function. It is known that patients undergoing colorectal surgery have a high risk of postsurgical infection. The capacity to restitute a colonic microbiota as soon as possible with a predominance of the probiotic protective strains can play a protective role during this critical moment.

The aim of this study is to demonstrate that it is possible to colonize the colon of a patient in the pen-surgical period with probiotic strains by administration as a dietary supplement before and after the operation, despite the special condition the patient to be treated is in. Usually patients are under a significant amount of stress, are under heavy antibiotic treatment, might suffer from an impaired immune system and/or are at a significant danger of being colonized by pathogenic and antibiotic resistant bacteria that appear more and more often in repeatedly sterilized environments such as hospitals.

Patients and Methods.

30 subjects suffering from colonic adenocarcinoma were enrolled in a double-blinded study and randomly distributed into three groups:

Group 1: Probiotics at high dose ($10^9$ cfu).
Group 2: Probiotics at low dose ($10^7$ cfu).
Group 3: placebo.

Treatment.

The treatments were composed of *Lactobacillus johnsonii* La1 and *Bifidobacterium* BB536 (both bacterial strains were present at the same cfu level in the two products) blended with maltodextrin. The placebo was maltodextrin only.

The treatments started 3 days before surgery, were stopped the day of the surgery and were resumed after surgery until 12 days after surgery.

Main Parameter.

The primary outcome of the study was the luminal or mucosal colonization assessed at the moment of surgery.

Results.

Group codes were A (placebo), B (probiotics at $10^7$) and C (probiotics at $10^9$). The colonization at DO (day of surgery) in colonic content or mucosal biopsy with *Lactobacillus johnsonii* La1 was demonstrated in 3 out of 11 patients in group B and in 4 out of 9 patients in group C.

TABLE 1

|  |  | Presence of bacteria in the colonic content or mucosal biopsy | |
|---|---|---|---|
|  |  | No | Yes |
| La1 | A | 10 | 0 |
|  | B | 8 | 3 |
|  | C | 5 | 4 |

Conclusions.

These results demonstrate that a typical probiotic, *Lactobacillus johnsonii* La1, is able to colonize the distal colon in patients that are undergoing colectomy due to colo-rectal adenocarcinoma. Patients suffering from these conditions and undergoing the surgical treatment are under stress and suffer from local major ecological modifications in the colon. Indeed colonic microbiota modifications occur as a result of dramatic alterations in the redox status of the colonic environment, antibiotic treatment and the intestinal lavage that gets rid of most of the iumenal biomass. The possibility to preserve a stable population of probiotic bacteria will create the basic condition for microbiota reconstitution. This in turn results in a better post-operation clinical condition of the patient by preventing infectious complications and by restoring the physiology of the colon that depends on a metabolically active microflora.

Example 2

A typical nutritional formulation prepared by the present invention is presented below:

The nutritional formulation is in this case a food preparation consisting of a mixture proteins, carbohydrates, fats, vitamins and minerals in amounts intended to meet 33% of the daily nutrient requirements of an adult person when 500 ml are consumed.

16% of the energy are provided by the protein fraction, 34% by the fats and 50% by the carbohydrates.

The protein source is 50% whey protein and 50% casein and the reconstituted powder contains 4 g of proteins per 100 ml (100 Kcal).

The lipid fraction is composed of rapeseed oil, medium chain triglycerides (MCT) and corn oil. MCT represent 25% of the lipids. The fatty acid profile is composed of 20% saturated fatty acids (FA), 40% monounsaturated fatty acids and 40% of polyunsaturated fatty acids. The n-6/n-3 fatty acid ratio is 4:1.

The carbohydrate content is 12.6 g per 100 ml of the reconstituted powder and is provided by maltodextrins. The product is lactose free.

The composition contains fibre provided by oligosaccharides (inulin) in a concentration of 1.5 g per 100 ml.

The powder contains spray dried *Lactobacillus johnsonii* La1 in a concentration of $10^8$ cfu per g of powder.

This standard reconstitution of the resulting product is 22 g of powder+84 ml of water for a serving of 100 ml.

The invention is claimed as follows:

1. A method comprising administering a composition comprising a probiotic to an adult patient scheduled to undergo surgery, the probiotic acts on the colon of the adult patient and is selected from the group consisting of *Lactobacillus johnsonii* La1 (CNCM I-1225), *Bifidobacterium longum* CNCM I-2170, *Bifidobacterium lactis* Bb12 (DSM20215), *Lactobacillus paracasei* CNCM I-2116, *Lactobacillus paracasei* CNCM I-1292, *Streptococcus faecium* SF 68, and combinations thereof.

2. The method of claim 1 wherein the composition is administered within three weeks of the surgery.

3. The method of claim 1 wherein the probiotic colonizes the colon of the adult patient.

4. The method of claim 1 wherein the composition modulates the immune system of the adult patient or stimulates production of mucosal secretory antibodies in the adult patient.

5. The method of claim 1 wherein the probiotic is selected from the group consisting of *Bifidobacterium longum* CNCM I-2170, *Bifidobacterium lactis* Bb12 and combinations thereof.

6. The method of claim 1 wherein the probiotic is selected from the group consisting of *Lactobacillus paracasei* CNCM I-2116, *Lactobacillus paracasei* CNCM I-1292, and combinations thereof.

7. The method of claim 1 wherein the probiotic comprises *Lactobacillus johnsonii* La1 (CNCM I-1225).

8. The method of claim 1 wherein the composition comprises a component selected from the group consisting of non-viable probiotic bacteria, probiotic-derived material and a combination thereof.

9. A method comprising administering a composition comprising a probiotic to an adult patient after surgery, the probiotic acts on the colon of the adult patient and is selected from the group consisting of *Lactobacillus johnsonii* La1 (CNCM I-1225), *Bifidobacterium longum* CNCM I-2170, *Bifidobacterium lactis* Bb12 (DSM20215), *Lactobacillus paracasei* CNCM I-2116, *Lactobacillus paracasei* CNCM I-1292, *Streptococcus faecium* SF 68, and combinations thereof.

10. The method of claim 9 wherein the composition is administered for a time period that comprises the day immediately after the surgery.

11. The method of claim 9 wherein the probiotic colonizes the colon of the adult patient.

12. The method of claim 9 wherein the adult patient has non-infectious diarrhea.

13. The method of claim 9 wherein the adult patient has infectious or toxigenic diarrhea.

14. The method of claim 9 wherein the adult patient has a nosocomial gastrointestinal infection.

15. The method of claim 9 wherein the composition modulates an inflammatory response during a healing process of the adult patient.

16. The method of claim 9 wherein the composition modulates the immune system of the adult patient or stimulates production of mucosal secretory antibodies in the adult patient.

17. The method of claim 9 wherein the probiotic is selected from the group consisting of *Bifidobacterium longum* CNCM I-2170, *Bifidobacterium lactis* Bb12 and combinations thereof.

18. The method of claim 9 wherein the probiotic is selected from the group consisting of *Lactobacillus paracasei* CNCM I-2116, *Lactobacillus paracasei* CNCM I-1292, and combinations thereof.

19. The method of claim 9 wherein the probiotic comprises *Lactobacillus johnsonii* La1 (CNCM I-1225).

20. The method of claim 9 wherein the composition comprises a component selected from the group consisting of non-viable probiotic bacteria, probiotic-derived material and a combination thereof.

* * * * *